US009924909B2

(12) United States Patent
Souchay (10) Patent No.: US 9,924,909 B2
(45) Date of Patent: Mar. 27, 2018

(54) SYSTEM AND METHOD FOR TOMOSYNTHESIS IMAGE ACQUISITION

(71) Applicant: General Electric Company, Schenectady, NY (US)

(72) Inventor: Henri Souchay, Versailles (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 261 days.

(21) Appl. No.: 14/817,591

(22) Filed: Aug. 4, 2015

(65) Prior Publication Data

US 2017/0035371 A1    Feb. 9, 2017

(51) Int. Cl.
*G01N 23/04* (2006.01)
*A61B 6/02* (2006.01)
*A61B 6/00* (2006.01)

(52) U.S. Cl.
CPC .............. *A61B 6/025* (2013.01); *A61B 6/502* (2013.01)

(58) Field of Classification Search
CPC ........ A61B 6/025; A61B 6/502; A61B 6/4452
USPC .................................................. 378/4–27, 37
See application file for complete search history.

(56) References Cited

U.S. PATENT DOCUMENTS

| | | |
|---|---|---|
| 5,594,769 A | 1/1997 | Pellegrino et al. |
| 5,999,836 A | 12/1999 | Nelson et al. |
| 6,256,370 B1 * | 7/2001 | Yavuz .................. G01N 23/046 378/22 |
| 6,282,264 B1 | 8/2001 | Smith et al. |
| 6,754,298 B2 | 6/2004 | Fessler |
| 6,940,943 B2 | 9/2005 | Claus et al. |
| 7,212,606 B2 | 5/2007 | Souchay et al. |
| 7,330,529 B2 | 2/2008 | Kautzer et al. |
| 8,207,736 B2 | 6/2012 | Chu et al. |
| 8,229,199 B2 | 7/2012 | Chen et al. |
| 8,246,543 B2 | 8/2012 | Johnson et al. |
| 8,284,894 B2 | 10/2012 | Poorter |
| 8,340,388 B2 | 12/2012 | Rosenstengel |
| 2008/0095420 A1 | 4/2008 | Ohyu et al. |
| 2009/0022264 A1 | 1/2009 | Zhou et al. |
| 2010/0128958 A1 | 5/2010 | Chen et al. |
| 2010/0284596 A1 | 11/2010 | Miao et al. |
| 2010/0303202 A1 | 12/2010 | Ren et al. |

(Continued)

FOREIGN PATENT DOCUMENTS

| | | |
|---|---|---|
| CN | 102867294 A | 1/2013 |
| EP | 0932363 A1 | 8/1999 |

(Continued)

OTHER PUBLICATIONS

European Search Report and Opinion issued in connection with corresponding EP Application No. 16181523.8 dated Dec. 9, 2016.

(Continued)

*Primary Examiner* — Courtney Thomas
(74) *Attorney, Agent, or Firm* — Grogan, Tuccillo & Vanderleeden, LLP (57) ABSTRACT

A method for image acquisition includes selectively concealing and exposing an x-ray source to a target object while the x-ray source travels along a first path, virtually moving an x-ray detector along a second path in a first direction while the x-ray source is exposed to the target object, and virtually moving the x-ray detector along the second path in a second direction generally opposite the first direction while the x-ray source is concealed from the target object.

19 Claims, 4 Drawing Sheets

(56) References Cited

U.S. PATENT DOCUMENTS

| | | |
|---|---|---|
| 2011/0062343 A1 | 3/2011 | Kato |
| 2011/0188624 A1 | 8/2011 | Ren et al. |
| 2012/0140878 A1 | 6/2012 | Souchay |
| 2012/0224664 A1 | 9/2012 | Maack |
| 2015/0332485 A1 | 11/2015 | Klausz et al. |
| 2016/0113607 A1 | 4/2016 | Souchay |

FOREIGN PATENT DOCUMENTS

| | | |
|---|---|---|
| EP | 2277446 A1 | 1/2011 |
| WO | 2008085577 A2 | 7/2008 |

OTHER PUBLICATIONS

Lyuboshenko et al., "Stable Signal and Image Reconstruction from Noisy Fourier Transform Phase", IEEE Transactions on Signal Processing, vol. No. 47, Issue No. 01, pp. 244-250, Jan. 1999.

Zhou et al., "Application of Fourier—Wavelet Regularized Deconvolution for Improving Image Quality of Free Space Propagation X-ray Phase Contrast Imaging", Physics in Medicine Biology, vol. No. 57, pp. 7459-7479, 2012.

PCT Search Report and Written Opinion issued in Connection With Related PCT Application No. PCT/US2015/030672 dated Sep. 15, 2015, 11 pages.

PCT Search Report and Written Opinion issued in Connection With Related PCT Application No. PCT/US2015/056463 dated Jan. 21, 2016, 11 pages.

\* cited by examiner

SYSTEM AND METHOD FOR TOMOSYNTHESIS IMAGE ACQUISITION

BACKGROUND

Technical Field

Embodiments of the invention relate generally to image acquisition. Particular embodiments relate to x-ray imaging systems used for mammography.

Discussion of Art

Generally, x-ray imaging systems expose an x-ray detector, e.g., gamma photon scintillator or film, to an x-ray source, via a target object that is to be imaged. Attenuation or dispersion of photons emitted from the x-ray source within the target object produces a variegated image at the x-ray detector. This image then can be processed to ascertain radiopacity at various regions of the target object. For example, in mammography, where breast tissue is imaged, a region of higher than average radiopacity is understood to indicate the presence of a potentially pre-cancerous or cancerous lesion.

In medical imaging, it is generally desirable to minimize the size and intensity of an x-ray source, especially when imaging radiation-sensitive tissues such as breast tissue. In particular, it is desirable to minimize the radiation exposure needed to identify and localize, in three dimensions, regions of high radiopacity that could indicate precancerous cells. To accomplish this, a moving x-ray source may be used to provide a low x-ray dose to the target tissue while also obtaining volumetric detector data for use in localizing regions of high radiopacity. A moving x-ray source, however, presents a potential problem of image distortion along the x-ray source direction of motion.

As mentioned, it is also desirable to identify radiopaque areas in three dimensions. Describing or displaying a three-dimensional structure from a sequence of planar images obtained from different perspectives is referred to as "tomosynthesis." The quality of tomosynthesis solutions depends upon the quantity and quality of planar images and on the total angle covered by the planar image array.

Tomosynthesis solutions generally can be categorized as "sharp" (providing relatively high resolution and fidelity of location within three dimensions) or "fast" (providing real-time or near-real-time imaging). For some types of medical imaging, such as mammography, sharp or fast solutions are exclusive choices. Fast tomosynthesis involves continuous source motion during exposure, therefore reducing signal transfer at higher frequencies, and loss of information, which precludes obtaining optimally sharp images. The fuzziness of fast tomosynthesis can be mitigated to some extent by a moving x-ray detector, however the final travel distance required for the detector eventually affects the possible imaging area due to positioning constraints of the patient/organ relative to the x-ray detector. Moreover, moving detectors typically require more complex mechanical assemblies and precise synchronization of mechanical parts, which increases system cost, as a whole.

In view of the above, it is desirable to provide apparatus and methods for moving source mammography that mitigates image distortion and provides for rapid image acquisition. Such apparatus and methods might also be helpful toward volumetric x-ray imaging, generally.

BRIEF DESCRIPTION

In an embodiment, a method for image acquisition includes selectively concealing and exposing an x-ray source to a target object while the x-ray source travels along a first path, virtually moving an x-ray detector along a second path in a first direction while the x-ray source is exposed to the target object, and virtually moving the x-ray detector along the second path in a second direction generally opposite the first direction while the x-ray source is concealed from the target object.

In another embodiment, an apparatus for image acquisition is provided. The apparatus includes an x-ray source moveable about a first path with reference to a target object, a static x-ray detector, and a control processor configured to selectively expose the x-ray source to the target object and conceal the x-ray source from the target object while the x-ray source is travelling about the first path, and virtually move the x-ray detector along a second path in a first direction while the x-ray source is exposed, and in a second direction, generally opposite to the first, when the x-ray source is concealed.

In yet another embodiment of the present invention, a method for image acquisition includes exposing an x-ray source to a target object while the x-ray source travels along a first path, virtually moving an x-ray detector along a second path in dependence upon movement of the x-ray source along the first path by digitally shifting a plurality of projection frames acquired during x-ray source exposure to the target object and, after digitally shifting the projection frames, combining a plurality of subsets of the projection frames to form a single super projection.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description. Although exemplary embodiments of the present invention are described with respect to mammography, embodiments of the invention also are applicable for use in volumetric imaging, generally. As will be appreciated, embodiments of the present invention may be used to analyze animal tissue generally and are not limited to human tissue.

As used herein, the terms "substantially," "generally," and "about" indicate conditions within reasonably achievable manufacturing and assembly tolerances, relative to ideal desired conditions suitable for achieving the functional purpose of a component or assembly.

Figure 1:
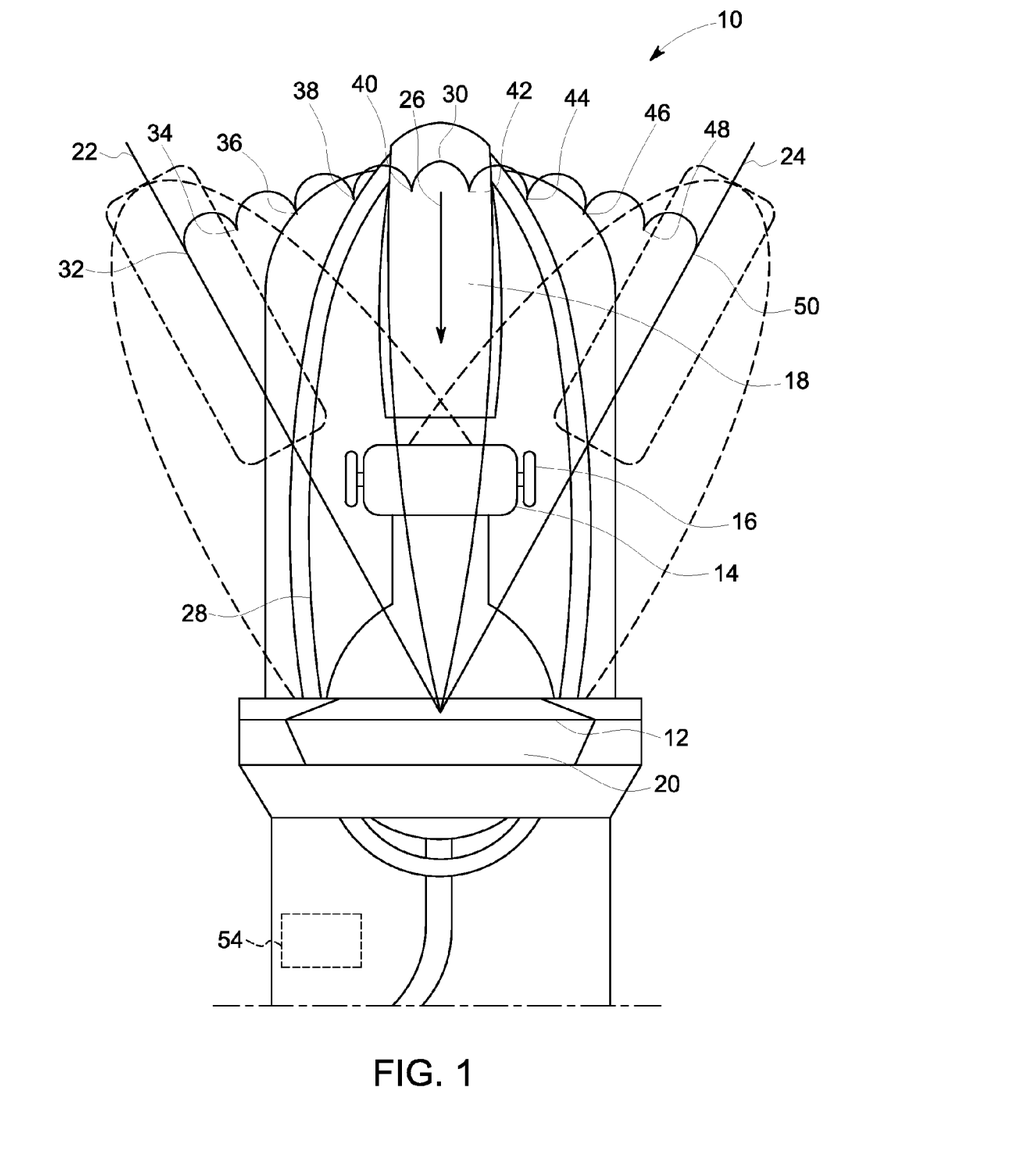
FIG. 1 depicts a radiographic projection tomography apparatus in accordance with an embodiment of the invention.

With reference to FIG. 1, a radiographic projection tomography apparatus 10 according to an embodiment of the present invention is illustrated. Tomography apparatus 10 includes support 12 that can support an object to be subjected to tomography. In an embodiment, the tomography apparatus 10 can be configured as a mammography apparatus wherein support 12 is a breast-holder support that supports a patient's breast. Nevertheless, any other type of tomography apparatus can be envisaged. Normally, the patient's breast is placed on the support and compressed by paddle 14 which can be maneuvered by an operator using for example handles 16. Tomography apparatus 10 furthermore comprises a source of radiation, such as x-ray emitting tube 18 and detector 20. The detector 20 is capable of detecting the rays after they have crossed the patient's breast. The detector 20 is placed beneath support 12. In practice, paddle 14 is made of an x-ray transparent material (e.g., plastic).

In accordance with one implementation, paddle 14, the patient's breast, support 12, and detector 20 are in fixed position, while the x-ray tube 18 may take up several positions in space relative to this assembly. In other implementations, the detector can travel in relation to the x-ray tube. In still other implementations, both the x-ray tube and the detector can move in a coordinated pattern relative to the patient's breast. Tomography device 10 includes a control processor 54 which executes computer readable instructions to control the operation of device 10.

In particular, FIG. 1 shows distributed in reorientation between a first extreme position 22 and a second extreme position 24 that are, for example, symmetrical relative to each other relative to a bisecting direction 26. The positions are on the whole distributed on an arc of a circle. In the depicted implementation, arm 28 carries tube 18. There are other possible arrangements enabling the tube and/or the detector to shift in a plane or a sphere portion.

Tube 18 is provided with focal spot 30 that is the x-ray emitting focal spot. For a multiplicity of exposure positions, herein represented by ten positions numbered 32 to 50, the number of these positions being greater than or equal to 3, is related to arranging a mammography device whose tube is at a halt at the incidence (position) 22 and, after regular exploration, is also at a halt at the incidence (position) 24.

On the path, the positions are distributed, preferably evenly, even though, with the image reconstruction processing corrections, it would be possible to envisage a case where the positions 32 to 50 are not evenly distributed. In accordance with one embodiment, image data can be sampled at regular intervals along the arc of motion, i.e., in and around the positions 32 to 50.

As can be seen in FIG. 1, especially when the motion of the focal spot is cycloid, the exact path of the focal spot is not necessarily that of an arc of a circle or of a sphere portion but is inscribed in a circular or spherical ring portion. However, the cycloid motion could be made in a plane or on a sphere portion. In this case, the relative motion would be tangential to this plane or to the surface of this sphere.

Figure 2A:
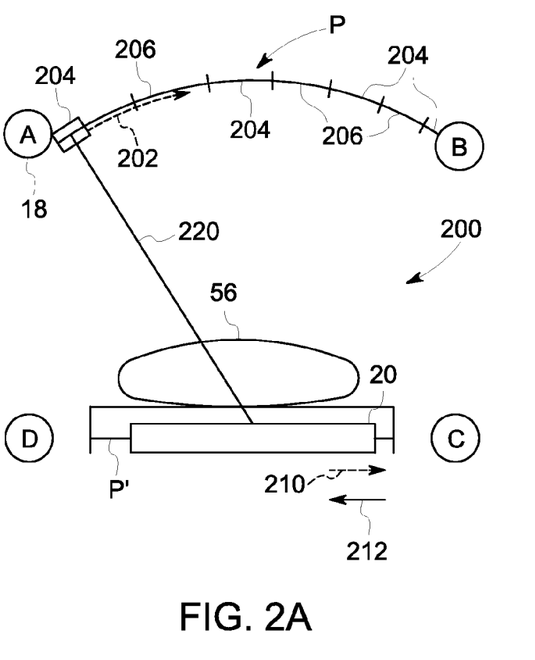
FIGS. 2A-2B show schematically a method of operating the apparatus shown in FIG. 1.
Figure 2B:
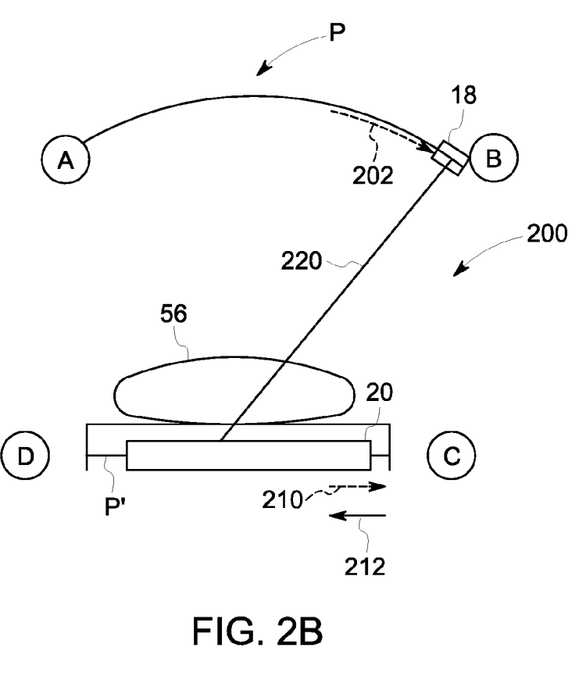

Referring to FIGS. 2A and 2B, during a mammography sequence 200, according to aspects of the invention, the control processor 54 implements movement 202 of the x-ray source 18 along a first path P, e.g., from a first position A toward a second position B. The total movement 202 may be continuous (scanning) or intermittent (snapshot). Embodiments in which the total movement 202 is a scanning movement advantageously reduce acceleration loads and cycles for which the x-ray source driver (not shown) must be designed. Although shown as arcuate, the path P, and movement 202, may be linear or plane-wise, e.g. sawtooth or curvilinear translational movement across a plane.

During the movement 202, the x-ray source 18 is intermittently exposed and concealed to the object 56 and the x-ray detector 20. In particular, the movement 202 comprises a first plurality of intervals 204 when the x-ray source 18 is exposed, as well as a second plurality of intervals 206 when the x-ray source is concealed. In order to enhance speed of operation and localization of radiopaque regions, at least the exposure intervals 204 provide continuous movement, in a "scanning" fashion without interruption or pauses.

According to certain embodiments, the concealment intervals 206 also provide continuous movement, so as to achieve the advantages of a total scanning movement 202 of the x-ray source 18 as discussed above. Although the exposure and concealment intervals 204, 206 are shown of generally equal length, they need not be equal in length and indeed a scanning movement can be accomplished with either type of interval being of arbitrary non-zero length.

In connection with the above, U.S. patent application Ser. No. 14/520,929, which is hereby incorporated by reference herein in its entirety, discloses a system and method for tomosynthesis image acquisition that reduces source blur by synchronizing the x-ray source motion with that of the detector in a manner that minimizes total x-ray detector travel. In particular, during exposure intervals, the control processor coordinates movement of the x-ray detector in order to match the scanning movements (e.g., movement 204) of the x-ray source, thereby minimizing variations of an apparent size of the x-ray source to the x-ray detector throughout exposure intervals. On the other hand, during concealment intervals, the control processor coordinates movement of the x-ray detector in order to reposition the x-ray detector relative to a photon beam from the x-ray source. More specifically, during image acquisition, the x-ray source is selectively concealed and exposed to the target object while the x-ray source travels along a first path, as discussed above. While the x-ray source is exposed to the target object, the x-ray detector is moved along a second path in a first direction. While the x-ray source is concealed from the target object, the x-ray detector is moved along the second path in a second direction generally opposite the first direction. Movement of the x-ray detector to match the scanning movements of the x-ray source, however, requires a more complex mechanical assembly and precise synchronization of mechanical parts, which increases the cost and complexity of the system, as a whole.

In order to achieve the benefits resulting from x-ray detector movement, namely, reducing source blur and minimizing the apparent size of the x-ray source to the x-ray detector, without increasing the cost and complexity of the system, the present invention proposes to instead employ a virtual movement of the x-ray detector 20 in order to match the scanning movements of the x-ray source 18. In particular, with further reference to FIGS. 2A and 2B, in addition to movement of the x-ray source 18, as described above, the control processor 54 also implements a virtual movement 208 of the x-ray detector 20 along a second path P' from a third position C toward a fourth position D and back. As used herein, "virtual movement" or "virtually move" means digitally shifting the projection frames at the control processor 54 to emulate detector motion.

In embodiments, the control processor 54 coordinates such virtual movement of the x-ray detector 20 with the scanning movement 202 of the x-ray source 18. During exposure intervals 204, the x-ray detector 20 is virtually moved generally along the second path in a first direction 212, i.e. from the third position C toward the fourth position D (i.e., the projection frames are digitally shifted so as to emulate actual detector motion). During concealment intervals 206, the x-ray detector 20 is moved virtually along the second path P' in a second direction 210 that is generally opposite the first direction, i.e. from the fourth position D back toward the third position C. Through this process, the control processor 54 may implement a generally oscillating motion of the x-ray detector 20. Although the movements 210, 212 are shown as linear, the x-ray detector 20 may be virtually moved in arcuate fashion about a common center with the x-ray source 18, as discussed hereinafter. Arcuate motion about a common center advantageously optimizes the apparent size of the x-ray source 18 to the x-ray detector 20.

In use, during exposure intervals 204, the control processor 54 coordinates the virtual movements 212 (i.e., digital shifting) of the x-ray detector 20 in order to match the plurality of scanning movements 204 of the x-ray source 18, thereby minimizing variations of an apparent size of the x-ray source 18 to the x-ray detector 20 throughout the exposure intervals 204. In an embodiment, during concealment intervals 206, the control processor 54 coordinates the virtual movements 210 (i.e., digital shifting) of the x-ray detector 20 in order to virtually reposition the x-ray detector 20 relative to a photon beam 220 from the x-ray source 18. The virtual or digital repositioning movements 210 can be directly oscillating, straight back toward the third position C; alternatively, the repositioning movements can be offset, so that the multiple poses are side-by-side rather than aligned along a line. In other embodiments the repositioning movements 210 can be more complex, e.g., curvilinear or elliptical.

In FIG. 2A, an embodiment of the inventive apparatus 10 is presented in schematic view at the beginning of the sequence 200. In FIG. 2B, the inventive apparatus 100 is presented in schematic view at the end of the sequence 200. Overall, the x-ray detector 20 is only virtually moved to a small extent, which virtual motion is coordinated with the movement of the exposed x-ray source 18 so that, during the exposure intervals 204, the apparent size of the x-ray source 18 as seen from the x-ray detector 20 through a fixed region of the target object, is preserved. In an embodiment, the distance of the virtual motion of the detector 20 can be adjusted as a function of object thickness to maximize the focusing effect.

In other words, during each of the exposure intervals 204, the x-ray source 18 and the x-ray detector 20 may be 'moved' together. In particular, as the x-ray source is moved from A toward B, the projection frames acquired are digitally shifted in a manner that emulates a corresponding detector motion from C toward D. The specific extent to which the projection frames are digitally shifted may be dictated by a control algorithm utilized by the control processor 54, similar to that disclosed in the '929 application.

In operation, the apparatus 10 acquires a series of x-ray images (projections) during the scanning movement 204 of the x-ray source. As discussed above, in an embodiment, the projections may be acquired during the exposure intervals 204. In other embodiments, the projections may be acquired continuously as disclosed in U.S. patent application Ser. No. 14/278,353, which is incorporated by reference herein in its entirety.

Once the projection frames are acquired, the control processor 54 processes (shifts) them digitally to emulate x-ray detector motion, as described above, on subsets of frames. Each subset of frames is then combined to form a single super-projection. The processing steps utilized to generate the super-projection may be similar to existing methods, such as those disclosed in the '353 application. Other conventional reconstruction architectures can also be utilized. Notably, however, the processing steps utilized by the control processor 54 are simplified as compared to existing methods, because only the super-projections are stored and processed. This is in contrast to existing methods with large numbers of images to reconstruct from. The present invention, therefore, reduces source blur by shifting virtually (digitally) multiple frames acquired rapidly, which are then summed into a single super-projection. In contrast to existing methods, the reconstruction architecture utilized by the control processor 54 only needs to handle a handful of projections instead of hundreds, thereby simplifying the reconstruction step.

Figure 3:
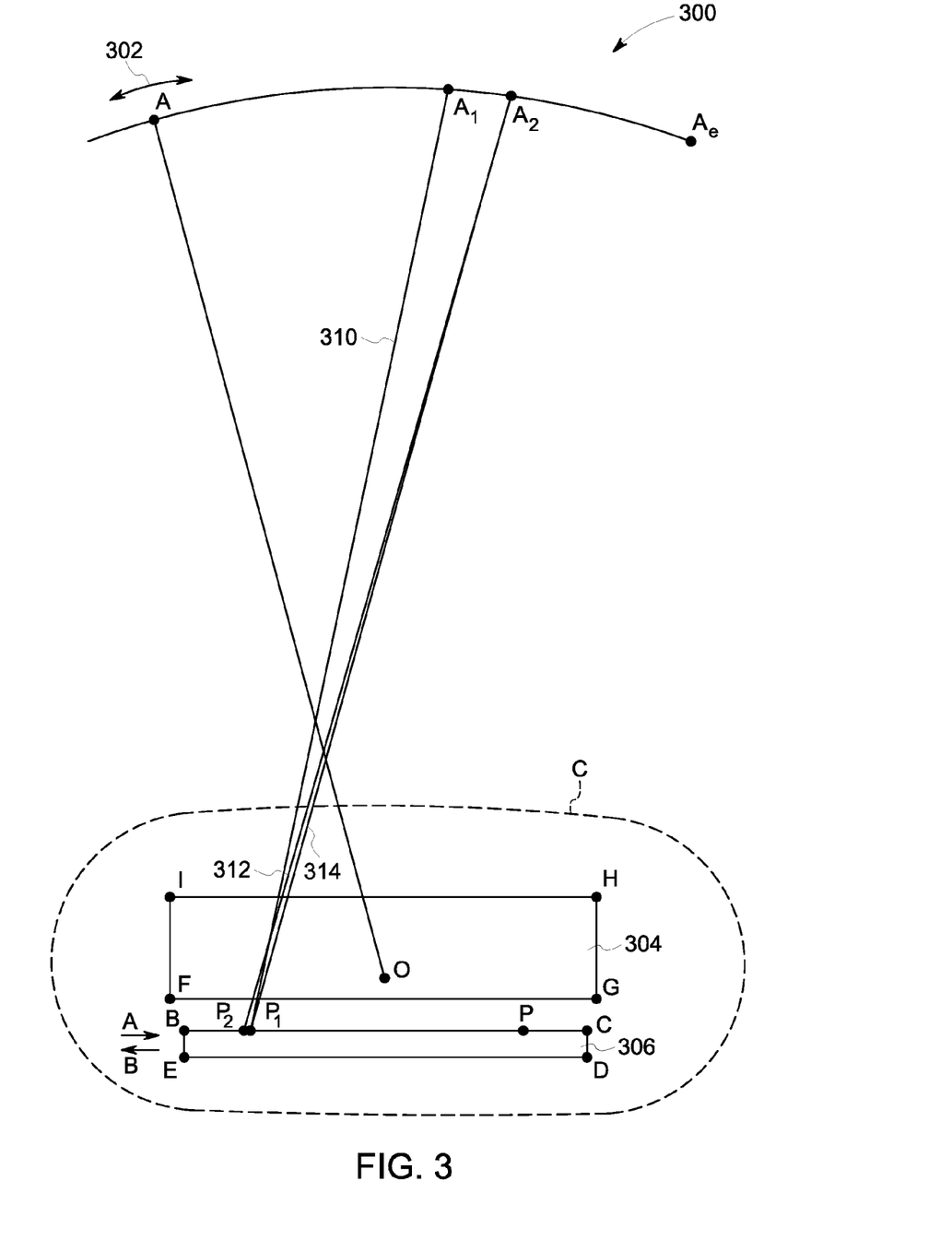
FIG. 3 illustrates a snapshot of a mammography sequence utilizing the tomography apparatus of FIG. 1.
Figure 4:
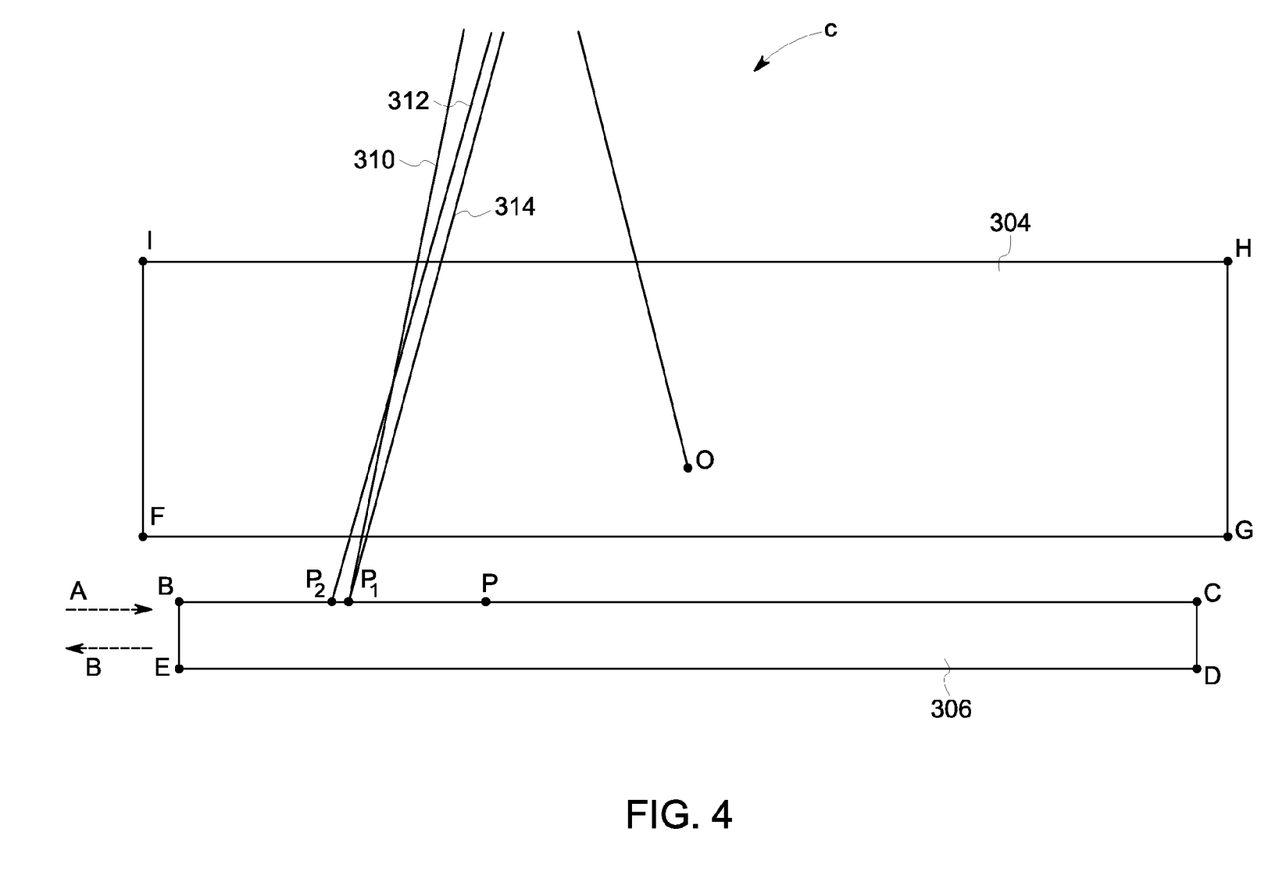
FIG. 4 is an enlarged view of area C of FIG. 3.

With reference to FIGS. 3 and 4, a snapshot of a mammography sequence 300 utilizing the apparatus 10 of the present invention is illustrated. As shown therein, 302 denotes the x-ray source trajectory from A to $A_e$ in relation to an object zone 304 containing a target object. As discussed above, the x-ray detector 306 is moved, virtually (digitally), in the direction of arrows A and B, along with the projection frames in order to reduce the apparent source size. Each time the detector 306 virtually strikes back to its start position, a super-projection is generated from the interim frames. In an embodiment, the processor is configured to impart a virtual rotation of the x-ray detector 306 about point O in dependence upon the movement of the x-ray source along trajectory 302, which essentially translates to an virtually oscillation of the x-ray detector in the direction of arrows A and B.

Turning now to FIG. 4, an enlarged view of area C of FIG. 3 illustrates the focusing effect of the virtual detector motion. Point P represents a typical projection point. P1 is the actual position of P at the beginning of a projection frame set, while P2 is the actual position of P at the end of a projection frame set. Line 310 (between P1A1) and line 312 (between P2A2) show the apparent source size inside the target volume 304 with the virtual moving detector 306, while line 310 (between P1A1) and line 314 (between P1A2) show the apparent source size inside the target volume 304 with a conventional, static detector. As will be readily appreciated, therefore, and as shown in FIG. 4, by virtually moving the detector (i.e., digitally shifting the projection frame subsets) as taught by the present invention, the apparent size of the x-ray source to the x-ray detector may be minimized. As illustrated in FIGS. 3 and 4, the A1A2 arc is acquired with multiple frames, each of which has negligible object blur. All frames are rapidly recombined into a single projection, compensating detector shift by shifting frames from one another.

The present invention, therefore, resolves the problem of fast tomosynthesis acquisition with currently available technology, at a reasonable cost. Moreover, in contrast to existing systems and methods, the present invention does not require a complex and robust reconstruction architecture because a small amount of projections are generated by the system. In addition, no new mechanical components or assemblies are required. In connection with the above, the technology generating high-speed acquisitions is readily available with CMOS detectors. The real-time shift and recombination of subsets of frames described above can be programmed on either a field-programmable gate array (FPGA) or a graphics processing unit (GPU). In connection with this, there is no need for any specialized detector assembly.

The present invention procures a fast tomosynthesis solution that utilizes readily available components and architectures, at reasonable cost. Exposure times in tomosynthesis may be reduced from 10 seconds to approximately 2 seconds. In an embodiment, the present invention is compatible with variable dose/variable speed sequences for more effective dose distribution schemes.

Thus, embodiments of the invention implement a method for image acquisition, which includes selectively concealing and exposing an x-ray source to a target object while the x-ray source travels along a first path, virtually moving an x-ray detector along a second path in a first direction while the x-ray source is exposed to the target object, and virtually moving the x-ray detector along the second path in a second direction generally opposite the first direction while the x-ray source is concealed from the target object. In an embodiment, virtually moving the x-ray detector includes digitally shifting a plurality of projection frames acquired during x-ray source exposure to the target object. The method may also include the step of combining a plurality of subsets of the projection frames to form a single super projection after digitally shifting the projection frames. In an embodiment, the first path is generally arcuate about an axis that is disposed between the x-ray source and the x-ray detector. In an embodiment, the second path includes at least one side stepping movement. The side stepping movements may correspond to when the x-ray source is concealed from the target object. In an embodiment, the selective concealing and exposing an x-ray source to a target object, while the x-ray source travels along the first path, occurs in a plurality of respective first and second intervals. In an embodiment, the method may also include the step of adjusting a distance of virtual motion of the x-ray detector in dependence upon a thickness of the target object.

In another embodiment, an apparatus for image acquisition is provided. The apparatus includes an x-ray source moveable about a first path with reference to a target object, a static x-ray detector, and a control processor configured to selectively expose the x-ray source to the target object and conceal the x-ray source from the target object while the x-ray source is travelling about the first path, and virtually move the x-ray detector along a second path in a first direction while the x-ray source is exposed, and in a second direction, generally opposite to the first, when the x-ray source is concealed. In an embodiment, the first path is generally arcuate about an axis that is disposed between the x-ray source and the x-ray detector. In an embodiment, the second path is generally linear and the first direction is generally contrary to the movement of the x-ray source, while the second direction is generally aligned with the movement of the x-ray source. In an embodiment, virtually moving the x-ray detector includes digitally shifting a plurality of projection frames acquired during x-ray source exposure to the target object. In an embodiment, the control processor is configured to combine a plurality of subsets of the projection frames to form a single super projection after digitally shifting the projection frames. In an embodiment, the second path may include one or more side stepping movements. The side stepping movements may correspond to when the x-ray source is concealed. In an embodiment, the control processor is housed within a stand supporting the x-ray source, the target receptacle, and the x-ray detector. In certain embodiments, the control processor incorporates a mechanism for coordinating the virtual movement of the x-ray detector along the second path with the movement of the x-ray source along the first path. In an embodiment, the control processor includes at least one of a field programmable gate array or a graphics processing unit. In an embodiment, the x-ray detector is a CMOS x-ray detector.

In yet another embodiment of the present invention, a method for image acquisition includes exposing an x-ray source to a target object while the x-ray source travels along a first path, virtually moving an x-ray detector along a second path in dependence upon movement of the x-ray source along the first path by digitally shifting a plurality of projection frames acquired during x-ray source exposure to the target object and, after digitally shifting the projection frames, combining a plurality of subsets of the projection frames to form a single super projection.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and apparatus, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for image acquisition, comprising the steps of:
   selectively concealing and exposing an x-ray source to a target object while the x-ray source travels along a first path;
   virtually moving an x-ray detector along a second path in a first direction while the x-ray source is exposed to the target object,
   virtually moving the x-ray detector along the second path in a second direction generally opposite the first direction while the x-ray source is concealed from the target object; and
   producing an image from data acquired during x-ray source exposure to the target object.

2. The method according to claim 1, wherein:
   virtually moving the x-ray detector includes digitally shifting a plurality of projection frames acquired during x-ray source exposure to the target object.

3. The method according to claim 2, further comprising the step of:
   combining a plurality of subsets of the projection frames to form a single super projection after digitally shifting the projection frames.

4. The method according to claim 2, wherein:
   the first path is generally arcuate about an axis that is disposed between the x-ray source and the x-ray detector.

5. The method according to claim 1, wherein:
   the second path includes at least one side stepping movement.

6. The method according to claim 5, wherein:
   the side stepping movements correspond to when the x-ray source is concealed from the target object.

7. The method according to claim 1, wherein:
   the selective concealing and exposing an x-ray source to a target object, while the x-ray source travels along the first path, occurs in a plurality of respective first and second intervals.

8. The method according to claim 1, further comprising the step of:
   adjusting a distance of virtual motion of the x-ray detector in dependence upon a thickness of the target object.

9. An apparatus for image acquisition comprising:
   an x-ray source moveable about a first path with reference to a target object;
   a static x-ray detector; and
   a control processor configured to selectively expose the x-ray source to the target object and conceal the x-ray source from the target object while the x-ray source is travelling about the first path, and virtually move the x-ray detector along a second path in a first direction while the x-ray source is exposed, and in a second direction, generally opposite to the first, when the x-ray source is concealed;
   wherein virtually moving the x-ray detector includes digitally shifting a plurality of projection frames acquired during x-ray source exposure to the target object; and
   wherein the control processor is configured to combine a plurality of subsets of the projection frames to form a single super projection after digitally shifting the projection frames.

10. The apparatus of claim 9, wherein:
    the first path is generally arcuate about an axis that is disposed between the x-ray source and the x-ray detector.

11. The apparatus of claim 9, wherein:
    the second path is generally linear and the first direction is generally contrary to the movement of the x-ray source, while the second direction is generally aligned with the movement of the x-ray source.

12. The apparatus of claim 9, wherein:
    the second path includes one or more side stepping movements.

13. The apparatus of claim 12, wherein:
    the side stepping movements correspond to when the x-ray source is concealed.

14. The apparatus of claim 9, wherein:
    the control processor is housed within a stand supporting the x-ray source, the target receptacle, and the x-ray detector.

15. The apparatus of claim 9, wherein:
    the control processor incorporates a mechanism for coordinating the virtual movement of the x-ray detector along the second path with the movement of the x-ray source along the first path.

16. The apparatus of claim 9, wherein:
    the control processor includes at least one of a field programmable gate array or a graphics processing unit.

17. The apparatus of claim 9, wherein:
    the x-ray detector is a CMOS x-ray detector.

18. A method for image acquisition, comprising the steps of:
    exposing an x-ray source to a target object while the x-ray source travels along a first path, defining an exposure interval of the x-ray source;
    virtually moving an x-ray detector along a second path in dependence upon movement of the x-ray source along the first path by digitally shifting a plurality of projection frames acquired during x-ray source exposure to the target object; and
    after digitally shifting the projection frames, combining a plurality of subsets of the projection frames to form a single super projection;
    wherein one said single super projection is formed after each exposure interval of the x-ray source.

19. The method according to claim 18, further comprising the step of:
    storing only the super projections.

* * * * *